United States Patent
Shan et al.

(10) Patent No.: US 8,614,251 B2
(45) Date of Patent: Dec. 24, 2013

(54) CRYSTALLINE FORM VI OF AGOMELATINE, PREPARATION METHOD AND APPLICATION THEREOF

(75) Inventors: Hanbin Shan, Shanghai (CN); Peng Zhang, Shanghai (CN); Zhedong Yuan, Shanghai (CN); Xudong Jiang, Shanghai (CN); Yu Huang, Shanghai (CN); Hubo Wang, Shanghai (CN); Xufeng Cao, Shanghai (CN); Xingdong Cheng, Shanghai (CN); Xiong Yu, Shanghai (CN)

(73) Assignee: Les Laboratories Servier, Suresnes Cedex (FR)

( * ) Notice: Subject to any disclaimer, the term of this patent is extended or adjusted under 35 U.S.C. 154(b) by 150 days.

(21) Appl. No.: 13/138,615

(22) PCT Filed: Mar. 9, 2010

(86) PCT No.: PCT/CN2010/070931
§ 371 (c)(1),
(2), (4) Date: Sep. 9, 2011

(87) PCT Pub. No.: WO2010/102554
PCT Pub. Date: Sep. 16, 2010

(65) Prior Publication Data
US 2012/0004313 A1    Jan. 5, 2012

(30) Foreign Application Priority Data
Mar. 10, 2009 (CN) .......................... 2009 1 0047329

(51) Int. Cl.
*A01N 37/18*    (2006.01)
*A61K 31/16*    (2006.01)
*C07C 233/00*    (2006.01)
*C07C 235/00*    (2006.01)
*C07C 237/00*    (2006.01)
*C07C 239/00*    (2006.01)

(52) U.S. Cl.
USPC ............................................ 514/613; 564/123

(58) Field of Classification Search
USPC ............................................ 514/613; 564/123
See application file for complete search history.

(56) References Cited

U.S. PATENT DOCUMENTS

2007/0238792 A1 * 10/2007 Delalleau et al. ............. 514/740

FOREIGN PATENT DOCUMENTS

| CN | 1907958 | 2/2007 |
|----|---------|--------|
| CN | 100445264 | 12/2008 |
| CN | 101429134 | 5/2009 |
| CN | 101585779 | 11/2009 |

OTHER PUBLICATIONS

International Preliminary Report on Patentability for PCT/CN2010/070931, Jun. 17, 2010.
U.S. Appl. No. 11/497,696, filed Aug. 2, 2006.
U.S. Appl. No. 11/497,776, filed Aug. 2, 2006.
U.S. Appl. No. 12/291,143, filed Nov. 6, 2008.
International Search Report for PCT/CN2010/070931 of May 13, 2010.

* cited by examiner

*Primary Examiner* — Sarah Pihonak
(74) *Attorney, Agent, or Firm* — Hueschen and Sage

(57) ABSTRACT

The invention provides a new crystalline form of agomelatine, preparation and use thereof. The X-ray powder diffraction diagram of the agomelatine crystalline form shows main peaks at the diffraction angles 2θ 11.13°, 11.82°, 17.49°, 18.29°, 19.48°, 19.72°, 20.50°, 21.76°, 22.54°, 22.97°, 24.56°, 25.36°, 27.16° and 31.93°. Said new crystalline form is characterized by high purity, stability and good reproducibility, and thus is advantageous for the pharmaceutical formulation. In addition, the stability and solubility of said crystalline form are also superior over the several existing crystalline forms.

6 Claims, 1 Drawing Sheet

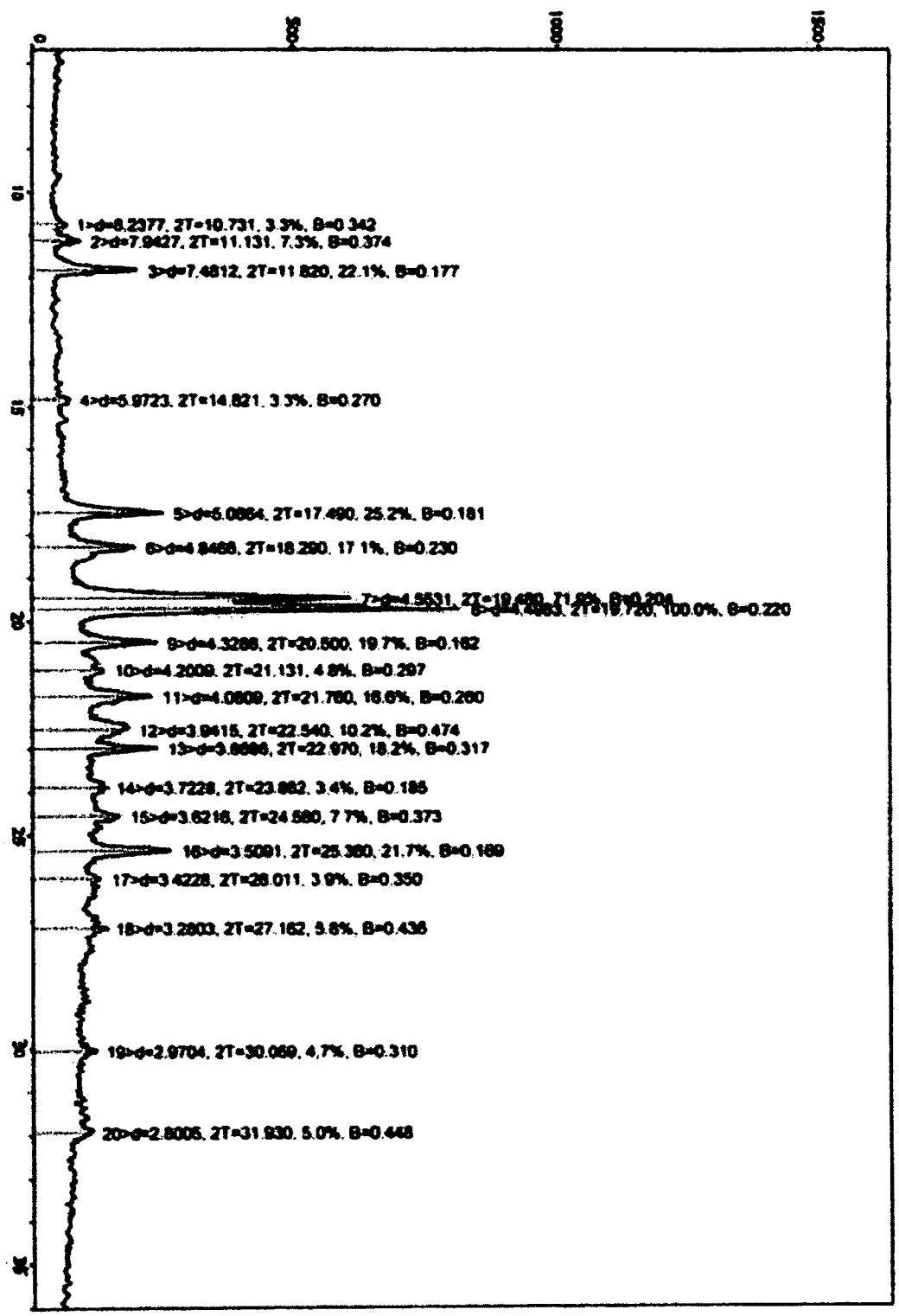

CRYSTALLINE FORM VI OF AGOMELATINE, PREPARATION METHOD AND APPLICATION THEREOF

TECHNICAL FIELD

The invention relates to a crystalline form of agomelatine, N[2-(7-methoxy-1-naphthyl)]acetamide, its preparation and use thereof.

TECHNICAL BACKGROUND

Agomelatine with chemical name N-[2-(7-methoxy-1-naphthyl)ethyl]acetamide and brand name Valdoxan has the following formula:

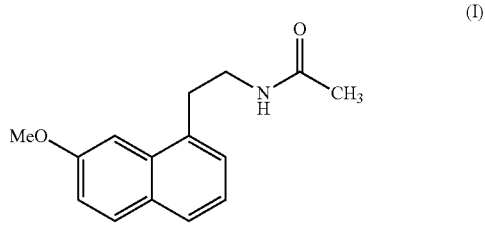 [SMILES: COc1ccc2cccc(CCNC(C)=O)c2c1]

Agomelatine has dual effects by acting as an agonist of melatoninergic system receptors and as an antagonist of the 5HT2C receptor. Its properties allow it to be active in the central nervous system, especially in the treatment of major depression, seasonal affective disorder, sleep disorder, cardiovascular diseases, diseases of the digestive system, insomnia and fatigue caused by jet lag, appetite disturbance and obesity. Agomelatine is the first melatoninergic antidepressant, and is effective for the treatment of depression, the improvement of sleep parameters and the maintenance of sexual function. The preparation and therapeutic use of agomelatine have been reported in the European patent EP0447285.

In view of the pharmaceutical value of agomelatine, it is critical to obtain the said compound in a highly pure, and stable crystalline form as well as with good reproducibility so that it will be advantageous in pharmaceutical formulations and stable enough for long-term storage without specific requirements regarding temperature, light, humidity or oxygen levels.

Chinese Patents CN200510071611.6, CN200610108396.7, CN200610108394.8 and CN200610108395.2 have respectively disclosed the crystalline forms II, III, IV, V of agomelatine and the preparations thereof.

Among these, crystalline form II is prepared by recrystallization from ethanol and water; crystalline form III is prepared by heating agomelatine at 110° C. until complete melting occurs and then slowly cooling down until formation of the crystal; crystalline form IV is prepared by heating agomelatine at 110° C. until complete melting occurs, followed by rapidly cooling down to 50-70° C. and maintaining at 70° C. for about 5 h until formation of the crystal occurs; crystalline form V is prepared by so-called "high-energy" mechanical grinding of agomelatine.

DESCRIPTION OF THE INVENTION

An objective of the invention is to provide a new crystalline form of agomelatine, i.e. crystalline form VI, which exhibits valuable characteristics in the pharmaceutical formulation.

Another objective of the invention is to provide a process for preparing crystalline form VI of agomelatine, which is simple to implement and easily reproducible.

The crystalline form of agomelatine, wherein the X-ray powder diffraction diagram of the crystalline form of agomelatine shows main peaks at the diffraction angles 2θ 11.13°, 11.82°, 17.49°, 18.29°, 19.48°, 19.72°, 20.50°, 21.76°, 22.54°, 22.97°, 24.56°, 25.36°, 271.6° and 31.93°.

The crystalline form of agomelatine, wherein the main peaks at the diffraction angles 2θ in the X-ray powder diffraction diagram of the crystalline form of agomelatine shows the following relative intensity (in percentages):

| 2θ° | Relative Intensity |
| --- | --- |
| 11.13 | 12.4 |
| 11.82 | 17.8 |
| 17.49 | 20.7 |
| 18.29 | 17.9 |
| 19.48 | 66.8 |
| 19.72 | 100 |
| 20.50 | 14.5 |
| 21.76 | 19.7 |
| 22.54 | 22.0 |
| 22.97 | 26.2 |
| 24.56 | 13.1 |
| 25.36 | 16.7 |
| 27.16 | 12.2 |
| 31.93 | 10.1 |

A process for preparing the crystalline form of agomelatine, wherein agomelatine is firstly dissolved in acetic acid and then added into 0-25° C. water to precipitate the crystal.

The process for preparing the crystalline form of agomelatine above, wherein the solution of agomelatine in acetic acid is most preferably added slowly to water with continuous stirring to facilitate the precipitation of the crystal. The said gradual addition to water may be achieved by dropwise addition.

The pharmacological studies with crystalline form VI of agomelatine according to the invention showed that the crystalline form VI of agomelatine may be used in the treatment of diseases of the melatoninergic system, sleep disorder, stress, anxiety, seasonal affective disorder or major depression, cardiovascular diseases, diseases of the digestive system, insomnia and fatigue caused by jet lag, schizophrenia, phobia, depression and the like.

The crystalline form VI of agomelatine provided according to the invention may be formulated together with various pharmaceutically acceptable adjuvants or excipients as various dosage forms for oral or injection administration.

According to the invention, the new crystalline form VI is obtained with high purity, stability and good reproducibility, and is advantageous for the pharmaceutical formulation. In addition, the stability and solubility of said crystalline form are also superior over the several existing crystalline forms.

BRIEF DESCRIPTION OF THE DRAWING

FIG. 1 is an X-ray diffraction diagram of the crystalline form VI obtained from Example 1 of the invention, measured by Bruker D8 ADVANCE instrument under the following settings: Cukα 40Kv 40 mA as light source, step length 0.02°, scan speed: 8°/min, scan range: 3°-80°, room temperature.

SPECIFIC EMBODIMENTS

Example 1

1 g of agomelatine was dissolved in 4 ml of acetic acid with stirring, then slowly added dropwise to 80 ml of water. The mixture was maintained at 0° C. with stirring for 3.5 h and filtered. The solid was washed with water 8 ml×2, dried at 55° C. under vacuum until the weight was constant to give 0.91 g of white solid. Purity: 99.6%, melting point: 97-98° C.

Example 2

1 g of agomelatine was dissolved in 4 ml of acetic acid with stirring, then slowly added dropwise to 80 ml of water. The mixture was maintained at 5° C. with stirring for 3 h and filtered. The solid was washed with water 8 ml×2, dried at 55° C. under vacuum until the weight was constant to give 0.90 g of white solid. Purity: 99.6%, melting point: 97-98° C.

Example 3

2 g of agomelatine was dissolved in 8 ml of acetic acid with stirring, then slowly added dropwise to 160 ml of water. The mixture was maintained at 20° C. with stirring for 3 h and filtered. The solid was washed with water 16 ml×2, dried at 55° C. under vacuum until the weight was constant to give 1.76 g of white solid. Purity: 99.6%, melting point: 97-98° C.

The crystalline form of agomelatine from Example 2 was dried to give a powdery product, whose X-ray diffraction diagram was plotted with interplanar spacing d, Bragg 2θ angle and relative intensity as follows:

| 2θ° | d(Å) | Relative Intensity |
|---|---|---|
| 11.13 | 7.942 | 12.4 |
| 11.82 | 7.481 | 17.8 |
| 17.49 | 5.066 | 20.7 |
| 18.29 | 4.846 | 17.9 |
| 19.48 | 4.553 | 66.8 |
| 19.72 | 4.498 | 100 |
| 20.50 | 4.328 | 14.5 |
| 21.76 | 4.080 | 19.7 |
| 22.54 | 3.941 | 22.0 |
| 22.97 | 3.868 | 26.2 |
| 24.56 | 3.621 | 13.1 |
| 25.36 | 3.509 | 16.7 |
| 27.16 | 3.280 | 12.2 |
| 31.93 | 2.800 | 10.1 |

Tests of Experimental Results

Crystalline forms II, III, IV and VI are respectively placed in a thermostatically controlled container at 40° C. for 20 days. The stability of the said crystalline forms is assessed by high performance liquid chromatography.

1. Purity Measurement of the Sample

Chromatographic conditions: octadecylsilane bonded silica as filler; a mixed solution of 10 mM/L phosphate buffer (adjusted to pH 7.0 by sodium hydroxide) and acetonitrile in 2:7 by volume as mobile phase; column temperature 40° C.; detection wavelength 220 nm. The purity is determined using an internal standard method.

The crystalline forms II, III, IV and VI were formulated with the mobile phase as 1 mg/mL solution. 10 μL of each of the solution was removed and injected into the liquid chromatograph. The chromatograms were recorded.

2. Assay of the Sample

The assay was carried out using an external standard method as described under Purity Measurement of the Sample. The results are as shown in Table I:

TABLE I

| Sample name | Purity of crystalline form II | Purity of crystalline form III | Purity of crystalline form IV | Purity of crystalline form VI |
|---|---|---|---|---|
| Before storage | 99.79% | 99.77% | 99.82% | 99.60% |
| After storage in the thermostatically controlled containers for 20 days | 99.24% | 99.10% | 99.54% | 99.55% |

3. Solubility Measurement in Water

The measurement was carried out by HPLC using an external standard method. The results are as shown in Table II:

TABLE II

| Sample name | Purity of crystalline form II | Purity of crystalline form VI |
|---|---|---|
| Purity | 99.79% | 99.77% |
| Solubility (mg/ml) | 1.11 | 1.24 |

From the above results, it is seen that the new crystalline form VI of agomelatine is superior over the several existing crystalline forms in terms of stability and solubility. With regard to its preparation, the new crystalline form is also of greater value than the existing crystalline forms III, IV and V in terms of industrial application.

The invention claimed is:

1. A crystalline form of agomelatine, having a powder X-ray diffraction diagram exhibiting peaks at diffraction angles 2θ 11.13°, 11.82°, 17.49°, 18.29°, 19.48°, 19.72°, 20.50°, 21.76°, 22.54°, 22.97°, 24.56°, 25.36°, 27.16° and 31.93°.

2. The crystalline form of agomelatine according to claim 1, wherein the peaks at the diffraction angles 2θ in the X-ray powder diffraction diagram exhibit the following relative intensities (in percentages):

| 2θ° | Relative Intensity |
|---|---|
| 11.13 | 12.4 |
| 11.82 | 17.8 |
| 17.49 | 20.7 |
| 18.29 | 17.9 |
| 19.48 | 66.8 |
| 19.72 | 100 |
| 20.50 | 14.5 |
| 21.76 | 19.7 |
| 22.54 | 22.0 |
| 22.97 | 26.2 |
| 24.56 | 13.1 |
| 25.36 | 16.7 |
| 27.16 | 12.2 |
| 31.93 | 10.1. |

3. A process for preparing the crystalline form of agomelatine according to claim 1, wherein agomelatine is first dissolved in acetic acid and then added into 0-25° C. water to precipitate the crystalline form.

4. The process according to claim 3, wherein the solution of agomelatine in acetic acid is added slowly to water with continuous stirring to facilitate the precipitation of the crystalline form.

5. A pharmaceutical composition comprising a crystalline form of agomelatine according to claim 1, together with one or more pharmaceutically acceptable adjuvants or excipients.

6. A pharmaceutical composition comprising a crystalline form of agomelatine according to claim 2, together with one or more pharmaceutically acceptable adjuvants or excipients.

* * * * *

UNITED STATES PATENT AND TRADEMARK OFFICE
CERTIFICATE OF CORRECTION

PATENT NO. : 8,614,251 B2
APPLICATION NO. : 13/138615
DATED : December 24, 2013
INVENTOR(S) : Hanbin Shan et al.

Page 1 of 1

It is certified that error appears in the above-identified patent and that said Letters Patent is hereby corrected as shown below:

Title Page, item [73] Assignee: "Les Laboratories Servier" should be --Les Laboratoires Servier--.

Signed and Sealed this
Twenty-fifth Day of February, 2014

Michelle K. Lee
*Deputy Director of the United States Patent and Trademark Office*